(12) United States Patent
Bailey et al.

(10) Patent No.: US 7,323,201 B2
(45) Date of Patent: Jan. 29, 2008

(54) HIGHLY SOLUBLE FORM OF TRICALCIUM CITRATE, AND METHODS OF ITS MAKING AND USE

(75) Inventors: Alexandria L. Bailey, Champaign, IL (US); Warren L. Nehmer, Decatur, IL (US); Roy O. Elmore, Atwood, IL (US)

(73) Assignee: Tate & Lyle Ingredients Americas, Inc., Decatur, IL (US)

( * ) Notice: Subject to any disclaimer, the term of this patent is extended or adjusted under 35 U.S.C. 154(b) by 609 days.

(21) Appl. No.: 10/863,616

(22) Filed: Jun. 8, 2004

(65) Prior Publication Data

US 2005/0271772 A1    Dec. 8, 2005

(51) Int. Cl.
*A23L 1/304* (2006.01)
(52) U.S. Cl. .................. 426/74; 426/516; 426/519; 426/520; 426/590; 426/599
(58) Field of Classification Search ................ 426/74, 426/590, 599, 658, 516, 519, 520
See application file for complete search history.

(56) References Cited

U.S. PATENT DOCUMENTS

| | | | | |
|---|---|---|---|---|
| 2,297,599 A | 9/1942 | Wilen | ............................ | 167/57 |
| 2,325,360 A | 7/1943 | Ayers et al. | ................... | 99/155 |
| 2,548,594 A | 4/1951 | Edmonds | ...................... | 99/105 |
| 2,845,355 A | 7/1958 | McColloch et al. | ........... | 99/155 |
| 2,851,360 A | 9/1958 | Diller | ............................ | 99/78 |
| 2,868,646 A | 1/1959 | Schapiro | ........................ | 99/78 |
| 2,985,562 A | 5/1961 | Millard et al. | ................. | 167/82 |
| 3,030,213 A | 4/1962 | Tidridge et al. | ............... | 99/129 |
| 3,114,641 A | 12/1963 | Cook et al. | .................... | 99/105 |
| 3,227,562 A | 1/1966 | Houghtaling et al. | ......... | 99/205 |
| 3,622,379 A | 11/1971 | Fehmerling | .................. | 117/118 |
| 3,639,278 A | 2/1972 | Hwa | ............................ | 252/82 |
| 3,639,279 A | 2/1972 | Gardner et al. | ................ | 252/86 |
| 3,657,424 A | 4/1972 | Aktins et al. | ................ | 424/153 |
| 3,939,289 A | 2/1976 | Hornyak et al. | ............. | 426/548 |

(Continued)

FOREIGN PATENT DOCUMENTS

DE          30 14 503          10/1981

(Continued)

OTHER PUBLICATIONS

GBI Marketing Information: www.tri-calcium-citrate.com/var/184/1583-TCC-VitD.pdf. No date given.*

(Continued)

*Primary Examiner*—Helen Pratt
(74) *Attorney, Agent, or Firm*—Williams, Morgan & Amerson, P.C.

(57) ABSTRACT

We report herein a composition comprising tricalcium citrate, wherein the tricalcium citrate has an X-ray powder diffraction pattern comprising peaks at 2-theta (2θ) values of about 8.236, about 16.02, about 17.97, about 19.75, about 21.42, about 25.74, and about 28.65. This tricalcium citrate is produced at high temperatures in a low-water environment. This composition is highly soluble (more than about 200 mg per 8 fluid ounces) in potable aqueous solutions (beverages), and can be used to fortify beverages (such as fruit juices) or foods with calcium at higher doses than seen when using previously-known compositions of tricalcium citrate.

8 Claims, 5 Drawing Sheets

U.S. PATENT DOCUMENTS

| | | | |
|---|---|---|---|
| 3,949,098 A | 4/1976 | Bangert | 426/324 |
| 3,965,273 A | 6/1976 | Stahl | 426/548 |
| 3,968,263 A | 7/1976 | Reussner | 426/250 |
| 4,078,092 A | 3/1978 | Nishiyama | 426/584 |
| 4,127,645 A | 11/1978 | Witzel et al. | 424/44 |
| 4,357,254 A | 11/1982 | Kapiloff et al. | 252/181 |
| 4,423,029 A | 12/1983 | Rizzi | 424/54 |
| 4,448,770 A | 5/1984 | Epting, Jr. | 424/153 |
| 4,452,703 A | 6/1984 | Ralston et al. | 210/698 |
| 4,496,470 A | 1/1985 | Kapiloff et al. | 252/181 |
| 4,551,342 A | 11/1985 | Nakel et al. | 426/548 |
| 4,592,909 A | 6/1986 | Winer et al. | 424/127 |
| 4,722,847 A | 2/1988 | Heckert | 426/74 |
| 4,737,375 A | 4/1988 | Nakel et al. | 426/590 |
| 4,786,510 A | 11/1988 | Nakel et al. | 426/74 |
| 4,786,518 A | 11/1988 | Nakel et al. | 426/531 |
| 4,814,177 A | 3/1989 | Walsdorf et al. | 424/464 |
| 4,830,862 A | 5/1989 | Braun et al. | 426/74 |
| 4,851,221 A | 7/1989 | Pak et al. | 424/693 |
| 4,867,977 A | 9/1989 | Gailly et al. | 424/687 |
| 4,871,554 A | 10/1989 | Kalala et al. | 426/74 |
| 4,872,919 A | 10/1989 | Bucher et al. | 134/3 |
| 4,919,963 A | 4/1990 | Heckert | 426/599 |
| 4,992,282 A | 2/1991 | Mehansho et al. | 426/72 |
| 4,994,283 A | 2/1991 | Mehansho et al. | 426/74 |
| 5,028,446 A | 7/1991 | Saleeb et al. | 426/590 |
| 5,075,499 A | 12/1991 | Walsdorf et al. | 562/590 |
| 5,118,513 A | 6/1992 | Mehansho et al. | 426/2 |
| 5,124,046 A | 6/1992 | Sherwood et al. | 210/699 |
| 5,128,374 A | 7/1992 | Kochanowski | 514/574 |
| 5,149,552 A | 9/1992 | Vidal et al. | 426/321 |
| 5,151,274 A | 9/1992 | Saltman et al. | 424/630 |
| 5,186,965 A | 2/1993 | Fox et al. | 426/74 |
| 5,225,221 A | 7/1993 | Camden et al. | 426/74 |
| 5,232,709 A | 8/1993 | Saltman et al. | 424/630 |
| 5,314,919 A | 5/1994 | Jacobs | 514/574 |
| 5,389,387 A | 2/1995 | Zuniga et al. | 426/74 |
| 5,401,524 A | 3/1995 | Burkes et al. | 426/590 |
| 5,445,837 A | 8/1995 | Burkes et al. | 426/74 |
| 5,468,506 A | 11/1995 | Andon | 426/74 |
| 5,474,793 A | 12/1995 | Meyer et al. | 426/599 |
| 5,817,351 A | 10/1998 | DeWille et al. | 426/74 |
| 5,820,903 A | 10/1998 | Fleury et al. | 426/74 |
| 5,834,045 A | 11/1998 | Keating | 426/74 |
| 5,851,578 A | 12/1998 | Gandhi | 426/590 |
| 6,039,986 A | 3/2000 | Mallangi et al. | 426/74 |
| 2002/0102331 A1 | 8/2002 | Chang et al. | 426/74 |
| 2003/0008054 A1 | 1/2003 | Gordon et al. | 426/573 |
| 2004/0009264 A1 | 1/2004 | Ballman et al. | 426/74 |

FOREIGN PATENT DOCUMENTS

| | | |
|---|---|---|
| EP | 0 515 110 | 11/1992 |
| EP | 0 588 498 | 3/1994 |
| GB | 597 936 | 2/1948 |
| WO | WO97/06785 | 2/1997 |
| WO | WO98/43487 | 10/1998 |

OTHER PUBLICATIONS

Dairy Products:the calcium challenge, Reprint form International Food ingredients No. 3, 2002.*

Klahorst, "Calcium's Role" (Jan. 2001).

"Health Beverages for the Ages," *Weeks Publishing Company* (Jun. 1997—Cover Story).

* cited by examiner

HIGHLY SOLUBLE FORM OF TRICALCIUM CITRATE, AND METHODS OF ITS MAKING AND USE

BACKGROUND OF THE INVENTION

The present invention relates generally to the field of food processing. More particularly, it concerns a new form of tricalcium citrate and methods of its making and use.

In man, calcium is essential for blood clotting, muscle contraction, nerve transmission, and bone and tooth formation and maintenance. The United States recommended daily allowance (USRDA) of calcium for men and women between the ages of 19 and 50 is 1000 mg/day, and is even higher for older prepubescent children, adolescents, and adults over 50. However, it is probable that millions of United States residents fail to ingest recommended levels of calcium. For example, according to the United States National Health and Nutrition Examination Survey, as reported on the World Wide Web at http://www.nichd.nih.gov/milk/whycal/enough_cal.cfm, accessed Apr. 28, 2004, only about half of males ages 9-19 and only about 20% of females ages 9-19 ingest recommended levels of calcium.

The most common dietary source of calcium is dairy products, such as milk, which contains about 0.12% calcium by weight. However, milk competes with (among other beverages) fruit juices, carbonated soft drinks, and noncarbonated soft drinks, which traditionally have little to no calcium content, as beverage choices for United States consumers. Further, people with lactose intolerance often choose to avoid dairy products. Other foods rich in calcium include dark green, leafy vegetables, such as spinach and broccoli, but not all consumers enjoy such vegetables.

In light of these recommendations and observations, there is interest in fortifying foods or beverages with calcium in the form of a calcium-containing compound. Fortifying a food or beverage to level of calcium comparable to that of milk requires consideration of the solubility, bioavailability, and taste profile of the calcium-containing compound.

To insure consistent levels of calcium per serving, the calcium-containing compound desirably is soluble or evenly dispersed through the food or beverage. For clear beverages, it is desirable that the calcium-containing compound provides little if any increase in the opacity of the beverage when dissolved therein. The solubility of the calcium-containing compound in the beverage will depend on the beverage's pH, acid content, protein content, bottling temperature, and storage temperature, and the nature of the calcium-containing compound, among other parameters.

The bioavailability of the calcium-containing compound is the ease (or lack of it) for the calcium therein to reach a site in the body where calcium performs a necessary or useful function. If ingested calcium is not absorbed to an appreciable extent, there is little to no benefit to calcium fortification. In general, bioavailability is positively correlated with solubility, i.e., the more soluble the calcium-containing compound, the greater its bioavailability.

To improve the commercial acceptance of the fortified food or beverage, it is desirable for the calcium-containing compound to have a neutral or a pleasing taste profile. A number of calcium-containing compounds have been found to impart unpleasant flavor or mouth-feel to foods or beverages fortified therewith.

One known fortification approach involves fortification of foods and beverages with calcium salts, including, but not limited to, calcium citrate malate, calcium malate, calcium citrate fumarate, calcium fumarate, calcium lactate, calcium gluconate, calcium carbonate, calcium phosphate, or calcium chloride, among others. Procter & Gamble (Cincinnati, Ohio) is a commercial supplier of at least some of the foregoing calcium salts.

Another technique for fortifying beverages with calcium involves tricalcium citrate as a calcium-containing compound. Tricalcium citrates are commercially available from Jungbunzlauer AG (Basel, Switzerland), Mallinckrodt (St. Louis, Mo.), and Tate & Lyle North America (Decatur, Ill.). Tricalcium citrate has a relatively neutral taste profile and a relatively high bioavailability compared to other calcium-containing compounds. However, the solubility of tricalcium citrate in beverages is relatively low; for example, the solubility is no more than about 0.2 g/L in water at 25° C.

It would be desirable to have calcium-fortified foods and beverages with higher doses of dissolved calcium.

SUMMARY OF THE INVENTION

In one embodiment, the present invention relates to a composition comprising tricalcium citrate, wherein the tricalcium citrate has an X-ray powder diffraction pattern comprising peaks at 2-theta ($2\theta$) values of about 8.236, about 16.02, about 17.97, about 19.75, about 21.42, about 25.74, and about 28.65.

In another embodiment, the composition can be prepared by a method comprising blending about 4 mole parts to about 2 mole parts calcium as calcium salt and about 2 mole parts anhydrous citric acid or citric acid monohydrate, to yield blended calcium salt and citric acid. The blended calcium salt and citric acid can be melted, in a low-water environment, to allow formation of tricalcium citrate. The present invention, in a further embodiment, relates to the composition prepared by this method.

In an additional embodiment, the composition can be dissolved in a beverage, in order to fortify the beverage with calcium.

In yet another embodiment, the composition can be dispersed in a food, in order to fortify the food with calcium.

We report herein that the composition can be used to fortify a beverage with calcium at more than about 200 mg of calcium per 8 fluid ounces of the beverage, such as doses of greater than about 300 mg of calcium per 8 fl. oz.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
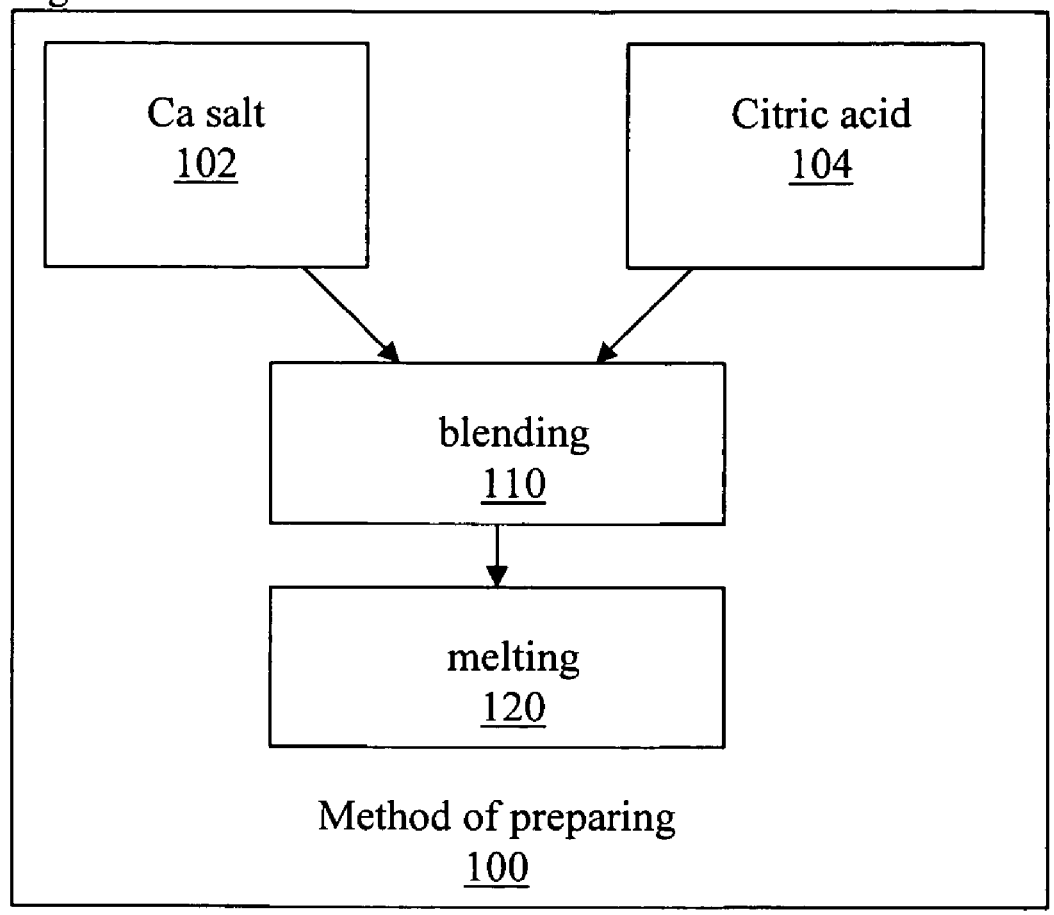
FIG. 1 shows a block diagram of a method of preparing a composition according to the present invention.

In one embodiment, the present invention relates to a composition comprising tricalcium citrate, wherein the tricalcium citrate has an X-ray powder diffraction pattern comprising peaks at 2-theta (2θ) values of about 8.236, about 16.02, about 17.97, about 19.75, about 21.42, about 25.74, and about 28.65.

In one embodiment, the X-ray powder diffraction pattern comprises peaks at 2θ values of 8.236 (0.02417), 16.02 (0.05443), 17.97 (0.03134), 19.75 (0.03062), 21.42 (0.02401), 25.74 (0.1259), and 28.65 (0.08219), wherein the parenthetical following each 2-theta value is the standard deviation.

When referring to the tricalcium citrate having the X-ray diffraction peaks discussed herein, the tricalcium citrate has a purity of at least 95 wt %, such as 95 wt %, 96 wt %, 97 wt %, 98 wt %, 99 wt %, or 100 wt %. Any impurities that may be present are not expected to have any significant impact on the 2θ location of the X-ray diffraction peaks of the tricalcium citrate.

The X-ray diffraction peaks and 2θ values can be determined by X-ray diffraction techniques that are well known in the art. We report an exemplary technique, although similar techniques, or variations in the present technique, can be used, as will be apparent to the skilled artisan having the benefit of the present disclosure. A glass capillary tube can be filled with a tricalcium citrate sample, sealed, and then exposed to X-rays. The exposure involved X-rays generated from copper atoms and thereafter collimated into a beam prior to impinging on and, for at least some X-rays, being scattered by the sample. (X-rays not scattered by the sample continued in line with the incident beam until absorbed by another part of the apparatus "downstream" from the sample). The scattered X-rays were collected on a beryllium detector plate over a 30° range of 2θ (wherein θ is the angle between the downstream beam line and a scattered X-ray) for 15 min. Thereafter, we integrated the scatter patterns over 2θ, graphed scatter intensity vs. 2θ, and observed peaks (local maxima in the curve of scatter intensity). We observed the tricalcium citrate of the present invention had different peaks in scatter intensity vs. 2θ than tricalcium citrates used commercially for calcium fortification of beverages. (Comparative data is presented in the examples, below).

As is well known to the skilled artisan, when X-rays impinge on a crystalline material from a particular incident angle, the crystalline material scatters the X-rays in a pattern determined by the crystal structure of the material. By observing the scatter pattern as a function of incident angle over a range of incident angles, the crystal structure of the material can be determined. The skilled artisan will be aware that the crystal structure of a material will correlate with its scatter intensity vs. 2θ plot. It is believed the crystal structure of the tricalcium citrate of the present invention differs from that of known tricalcium citrates.

The composition can consist of the tricalcium citrate of the present invention. Alternatively, the composition can comprise the tricalcium citrate and other materials. In one embodiment, the other materials are selected from those approved for use as a food additive or are GRAS (generally regarded as safe) under the laws or regulations of the United States or other jurisdiction.

The word "or," as used herein, has the inclusive meaning (i.e., the same meaning as the colloquial "and/or"), unless specified to the contrary.

In one embodiment, the composition further comprises a beverage stabilizer. Exemplary beverage stabilizers include sugars (e.g., sucrose, glucose, dextrose, fructose, high fructose corn syrup, or invert sugar, among others) or polysaccharides (e.g., pectin, algin, starch, hydrolyzed starch, xanthan gum, or other edible gum, among others), among others, as well as combinations of two or more beverage stabilizers. For example, a maltodextrin having a dextrose equivalent (DE) of from about 5 to about 15, such as about 10, can be used. The DE of a carbohydrate sample can be calculated by a known method, such as saccharide distribution by HPLC, among others.

When the composition further comprises a carbohydrate, the composition can comprise less than about 50 dry wt % of the carbohydrate. The dry wt % is determined over the total of all non-aqueous materials in the composition (i.e., dsb %). In one embodiment, the composition can comprise less than about 30 dry wt % of the carbohydrate. In a further embodiment, the composition can comprise less than about 15 dry wt % of the carbohydrate.

Other materials which can be included in the composition include, but are not limited to, organic acids, such as citric acid, malic acid, fumaric acid, or lactic acid, among others. Organic acids may be present in the composition as a result of conversion of citric acid to the organic acids during processing of the composition, such as at high temperatures.

In another embodiment, the present invention relates to a beverage, comprising a composition as described above.

The beverage can be any potable aqueous solution. Exemplary beverages include, but are not limited to, fruit juices (such as apple juice, orange juice, grapefruit juice, grape juice, tomato juice, or cranberry juice, among others), vegetable juices, fruit or vegetable juice medleys or cocktails, carbonated soft drinks (such as colas, lemon-lime carbonated soft drinks, club soda, or tonic water, among others, and including those containing either caloric sweeteners or non-caloric sweeteners and those either containing caffeine or not containing caffeine), non-carbonated soft drinks (including those containing either caloric sweeteners or non-caloric sweeteners and those either containing caffeine or not containing caffeine), coffee, coffee-based beverages (such as espresso, cappuccino, or other beverages comprising espresso, among others, and including both hot, iced, or blended frozen embodiments), coffee additives (such as dairy creamers or non-dairy creamers, among others), tea, tea-based beverages, tea additives, milk, sports drinks, so-called energy drinks, alcoholic beverages (such as beer, malted beverages, wine, sparkling wine, fortified wine, liquors, or pre-assembled liquor-based cocktails, among others), alcoholic beverage additives (such as margarita mix, sweet-and-sour mix, Collins mix, or daiquiri mix, among others), water fortified with one or more vitamins or minerals, sparkling water, or water, among others. The foregoing list is not to be construed as exhaustive or limiting.

In one embodiment, the beverage is apple juice or orange juice. In another embodiment, the beverage is a non-carbonated, non-calorically-sweetened soft drink.

The beverage can comprise any amount of the composition. In one embodiment, the beverage can comprise more than about 200 mg of calcium per 8 fluid ounces of the beverage, wherein the calcium is in the form of the tricalcium citrate of the present invention. In further embodiments, the beverage can comprise more than about 300 mg of calcium per 8 fluid ounces of the beverage, more than about 400 mg of calcium per 8 fluid ounces of the beverage, or more than about 500 mg of calcium per 8 fluid ounces of the beverage.

In another embodiment, the present invention relates to a food, comprising a composition as described above.

Exemplary foods include meats, vegetables, fruits, starches, and baked goods, whether fresh, canned, or frozen; canned or reconstituted soups; spices and stocks; and pre-packaged meals, snacks, and desserts; among others.

The food can comprise any amount of the composition. In one embodiment, the food can comprise more than about 200 mg of calcium per 2 ounces of the food.

In another embodiment, the present invention relates to a method of preparing a composition as described above. In another embodiment, the composition can be prepared by a method comprising blending about 4 mole parts to about 2 mole parts calcium as calcium salt and about 2 mole parts anhydrous citric acid or citric acid monohydrate, to yield blended calcium salt and citric acid; and melting the blended calcium salt and citric acid, in a low-water environment, to allow formation of tricalcium citrate. The anhydrous citric acid or citric acid monohydrate may be referred to, in describing this embodiment, as "citric acid."

FIG. 1 shows a block diagram of the method of preparing 100.

In the blending step 110, the calcium salt 102 and the anhydrous citric acid or citric acid monohydrate 104 can be blended by any appropriate technique. In one embodiment, about 3 mole parts calcium as calcium salt 102 and about 2 mole parts anhydrous citric acid or citric acid monohydrate 104 can be blended.

Any calcium salt 102 can be used. In one embodiment, the calcium salt 102 is approved for use as a food additive or is GRAS (generally regarded as safe) under the laws or regulations of the United States or other jurisdiction. However, because a large percentage of the calcium salt 102 will react with the citric acid 104, the calcium salt 102 need not be approved as a food additive or be GRAS, depending on the laws or regulations of any particular jurisdiction and the particular use for which the composition is intended. In one embodiment, the calcium salt 102 can be calcium hydroxide, calcium carbonate, or calcium oxide.

Citric acid 104 is known. In one embodiment, the citric acid 104 is anhydrous, that is, has substantially zero water molecules associated with it via hydrogen bonding interactions. In one embodiment, the citric acid 104 is a monohydrate, that is, has from substantially zero mole parts up to about one mole part of water associated with one mole part of the citric acid via hydrogen bonding interactions. In one embodiment, the citric acid 104 is granular, which denotes a particle size of less than about 1000 microns.

In one embodiment, "about 2 mole parts anhydrous citric acid or citric acid monohydrate" means from 1.9 mole parts anhydrous citric acid or citric acid monohydrate 104 to 2.1 mole parts anhydrous citric acid or citric acid monohydrate 104.

Blending can be performed by any technique known in the art. The blending step 110 yields blended calcium salt and citric acid.

The blended calcium salt and citric acid can then, in the melting step 120, be melted, by which is meant the citric acid 104 is rendered molten. The calcium salt 102 can also be rendered molten, or it can be rendered as a solute or suspended material within the molten citric acid phase. The melting step 120 can be performed in a low-water environment, by which is meant a reaction environment in which water is present at less than about 50 wt % of the reaction environment contents. In one embodiment, water is present at less than about 20 wt %. In a further embodiment, water is present at less than about 5 wt %.

In one embodiment, water has not been added as either a solid, a liquid, or a gas, except for any water vapor which may be present in the gas phase of the environment and any liquid or gaseous water present in the reactants as a result of accepted processes for manufacturing the reactants.

In one embodiment, the melting step comprises heating the blended calcium salt and citric acid to a temperature greater than about 150° C. at atmospheric pressure. The melting step 120 allows formation of tricalcium citrate. Heating can be performed in any apparatus capable of raising the blended calcium salt and citric acid to, and maintaining the blend at, a suitable temperature. Preferably, the apparatus is also capable of further mixing or blending to maintain or impart substantial homogeneity to the blended calcium salt and citric acid. In one embodiment, the melting step 120 is performed in an extruder. In another embodiment, the melting step 120 is performed in a mixer having a heating jacket.

In one embodiment of the melting step 120, any temperature greater than about 150° C. can be used, and the melting step 120 can have any duration. In one embodiment, the temperature and the duration of the melting step 120 can be sufficient to substantially completely react the calcium salt with the citric acid to form tricalcium citrate. Completeness of reaction can be determined as substantially all of the calcium salt in the reaction vessel being depleted and substantially all calcium in the reaction vessel being in the form of tricalcium citrate. Excess anhydrous citric acid or citric acid monohydrate can be present when the reaction is complete. As will be apparent to the skilled artisan, the precise temperature and the duration of the melting step 120 are a matter of routine experimentation, in light of the present disclosure. In one embodiment, the duration of the melting step 120 can be from about 5 sec to about 6 hr. In a further embodiment, the duration of the melting step 120 can be less than about 10 sec.

In one embodiment, the melting step 120 comprises heating at a temperature from about 175° C. to about 185° C. In one embodiment, the melting step 120 comprises heating under atmospheric pressure.

The product of the melting step 120 is a tricalcium citrate, along with a byproduct of reaction between anions from the calcium salt and protons from the citric acid (e.g., when the calcium salt is calcium hydroxide, the byproduct is water). The tricalcium citrate may comprise a small proportion (such as less than about 5 wt %) of impurities, such as organic acids, among others. Though not to be bound by theory, we submit the melting step 120 as described above leads to a tricalcium citrate having the crystalline structure defined by the X-ray powder diffraction 2θ peaks described above.

The blending step 110 and melting step 120 can be performed simultaneously.

During melting, other materials, such as those described above as suitable for use in the composition of the present invention, can be blended with the tricalcium citrate. In one embodiment, a beverage stabilizer can be blended with the tricalcium citrate. In a further embodiment, the beverage stabilizer is maltodextrin. In another embodiment, up to about 1 part by weight of the beverage stabilizer can be blended with about 1 part by weight tricalcium citrate. In a further embodiment, about 0.11 parts by weight of the beverage stabilizer can be blended with about 1 part by weight tricalcium citrate.

After melting and inclusion of any other material, the tricalcium citrate can be cooled, if desired; purified from the byproduct, if desired; or milled, if desired. Milling can be useful to generate a tricalcium citrate composition suitable for dissolving in a beverage or other further processing.

In another embodiment, the present invention relates to a method of fortifying a beverage with calcium, comprising:

dissolving (i) a composition comprising tricalcium citrate, wherein the tricalcium citrate is as described above, in (ii) the beverage.

The composition and the beverage can be as described above.

Figure 2:
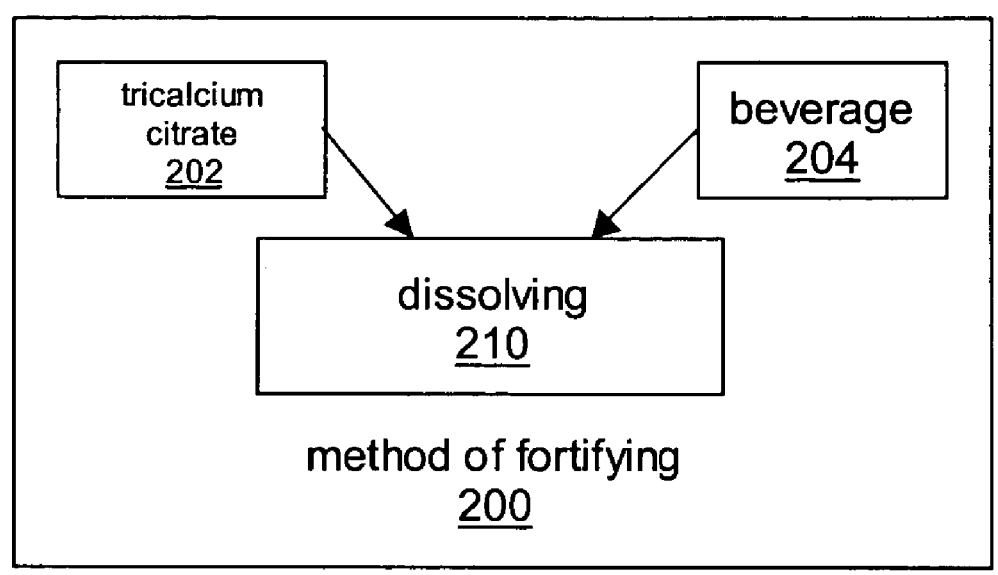
FIG. 2 shows a block diagram of a method of fortifying a beverage with calcium according to the present invention.

FIG. 2 shows a block diagram of the method of fortifying 200.

In the dissolving step 210, "dissolving" has its plain meaning. The dissolving step can be aided by the use of heat, agitation, cosolvents, or other techniques known in the art or any combination of two or more of the foregoing. The tricalcium citrate composition 202 and the beverage 204 can be as described above.

By use of the tricalcium citrate of the present invention, in some embodiments the method 200 can generate beverages comprising more than about 200 mg of calcium per 8 fluid ounces of the beverage, such as 300 mg of calcium per 8 fluid ounces of the beverage, 400 mg of calcium per 8 fluid ounces of the beverage, or 500 mg of calcium per 8 fluid ounces of the beverage.

The fortified beverage can then undergo further processing by techniques known in the art, if need be, and then be provided to the consumer in a retail setting.

In another embodiment, the present invention relates to a method of fortifying a food with calcium, comprising:

dispersing (i) a composition comprising tricalcium citrate, wherein the tricalcium citrate is as described above, in (ii) the food.

The composition and the food can be as described above.

Figure 3:
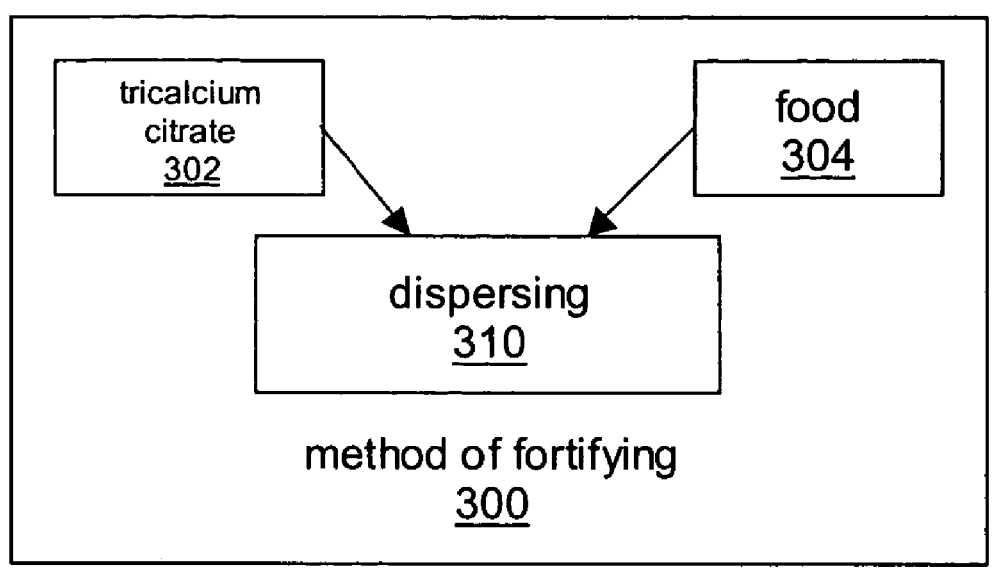
FIG. 3 shows a block diagram of a method of fortifying a food with calcium according to the present invention.

FIG. 3 shows a block diagram of the method of fortifying 300.

In the dispersing step 210, "dispersing" has its plain meaning. The dispersing step can be aided by the use of comminution, dry mixing, wet mixing, agitation, solvent treatment, or other techniques known in the art or any combination of two or more of the foregoing. The tricalcium citrate composition 302 and the food 304 can be as described above.

By use of the tricalcium citrate of the present invention, in some embodiments the method 300 can generate foods comprising more than about 200 mg of calcium per 2 ounces of the food.

The fortified food can then undergo further processing by techniques known in the art, if need be, and then be provided to the consumer in a retail setting.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Production of Tricalcium Citrate by Extrusion

Tricalcium citrate compositions were prepared by the following technique.

$Ca(OH)_2$ and anhydrous fine granular citric acid (mole ratio about 3:2) were blended together. In some embodiments, the $Ca(OH)_2$ and citric acid were blended along with Star-Dri® 10 maltodextrin at 10% dsb. The blend was then fed to a six-zone Leistritz ZSE-18/HP Laboratory Twin Screw Extruder. The extruder's zone temperatures were: Zone 1, 20° C.; Zone 2, 20° C.; Zone 3, 20° C.; Zone 4, 175° C.; Zone 5, 185° C.; and Zone 6, 180° C. Only the conveying screws were used, at 100 rpm. The feed rate was 9 g/min. The product was collected and cooled, and then milled over a 0.5 mm mesh screen using a Thomas mill.

EXAMPLE 2

Tricalcium Citrate Produced by Reactive Agglomeration

Tricalcium citrate compositions were prepared by the following technique.

$Ca(OH)_2$ and anhydrous fine granular citric acid (mole ratio about 3:2) were blended together. The blend was fed to a Littleford mixer equipped with a steam or oil heating jacket and heated to at least 150° C. The blend melted and the $Ca(OH)_2$ and citric acid reacted. The blend was mixed in the mixer for several minutes, to allow the reaction to go to completion, and then removed and milled.

EXAMPLE 3

Evaluation of Extruded and Reactive Agglomerated Tricalcium Citrate in Beverages Tricalcium citrate (TCC) samples prepared according to Example 1 or 2 were dissolved in beverages and subjected to various tests and observations. Specifically, the TCC was added to apple juice or orange juice until the beverage was saturated. The beverage was then refrigerated 24 hr to allow settling of insoluble particulates, leaving behind a beverage supernatant comprising dissolved TCC. Then, 15 g of the beverage supernatant was collected and centrifuged at 3000 rpm for 5 min. About 1.5 g-2 g of the centrifuge supernatant was filtered through a 0.45 μm nylon filter and placed in a flask; 0.5 mL of nitric acid was added; and the total volume was brought up to 100 mL with distilled water. Filtered liquid was analyzed for calcium content by axial view ICP using a Perkin Elmer Optima 4300 DV Optical Emission Spectrometer.

Results are shown in the following tables.

Table 3-1 shows calcium solubility for various TCC samples in commercially-available Musselman's Apple Juice.

TABLE 3-1

| Solubility of TCC Samples in Apple Juice | | |
|---|---|---|
| Calcium Source | Initial mg Ca/8 fl. Oz. | pH after addition |
| Extruded Tricalcium with 10% SD10 | 450 | 3.9 |
| Extruded Tricalcium Citrate | 500 | 3.9 |
| Reactive Agglomerated Tricalcium Citrate | 500 | 3.9 |

SD10, Star-Dri 10 maltodextrin

Table 3-1 shows that TCC samples prepared according to Examples 1 and 2 can be used to prepare apple juice fortified with about 450-500 mg Ca/8 fl. oz.

Table 3-2 shows calcium solubility for various extruded TCC samples in commercially-available Minute Maid Original Orange Juice.

TABLE 3-2

Solubility of TCC Samples in Orange Juice

| Calcium Source | Initial mg Ca/8 fl. Oz. | pH after addition |
|---|---|---|
| Extruded Tricalcium with 10% SD10 | 425 | 4.0 |
| Extruded Tricalcium Citrate | 500 | 4.0 |
| Reactive Agglomerated Tricalcium Citrate | 500 | 4.0 |

Table 3-2 shows that TCC samples prepared according to Examples 1 and 2 can be used to prepare orange juice fortified with about 425-500 mg Ca/8 fl. oz.

Table 3-3 shows the calcium solubility of TCC samples in apple juice before and after twelve weeks of storage at room temperature (25° C.) or at refrigerated temperature (4° C.). To minimize microorganism growth during the storage study, 0.6 wt/wt % benzoic acid was added to each sample.

TABLE 3-3

Calcium Solubility Study in Apple Juice

| Sample | Solubility (mg/8 fl. oz.) Stored at Room Temperature Initial | After 12 weeks | % Change In Solubility | Solubility (mg/8 fl. oz.) Stored at Refrigeration Temp Initial | After 12 weeks | % Change In Solubility |
|---|---|---|---|---|---|---|
| Extruded Tricalcium Citrate with Maltodextrin | 444 | 450 | 1.35 | 544 | 451 | −17.09 |
| Extruded Tricalcium Citrate | 515 | 461 | −10.49 | 535 | 484 | −9.53 |
| Reactive Agglomerated Tricalcium Citrate | 510 | 434 | −14.9 | 496 | 449 | −9.48 |

Table 3-3 shows that TCC samples prepared according to Examples 1 and 2 can be used to prepare apple juice fortified with about 450-550 mg Ca/8 fl. oz., and that the fortified apple juice can maintain at least about 80% of the initial calcium level in solution after about 12 weeks at either room temperature or about 4° C.

Table 3-4 shows the calcium solubility of TCC samples in orange juice before and after twelve weeks of storage at refrigerated temperature (4° C.). To minimize microorganism growth during the storage study, 0.6 wt/wt % benzoic acid was added to each sample.

TABLE 3-4

Calcium Solubility Study in Orange Juice

| Sample | Solubility (mg/8 fl. oz.) when stored at Refrigeration Temp Initial | After 12 weeks | % Change In Solubility |
|---|---|---|---|
| Extruded Tricalcium Citrate with Maltodextrin | 457 | 448 | −1.91 |
| Extruded Tricalcium Citrate | 514 | 353 | −31.43 |
| Reactive Agglomerated Tricalcium Citrate | 564 | 363 | −35.60 |

Table 3-4 shows that TCC samples prepared according to Examples 1 and 2 can be used to prepare orange juice fortified with about 450-570 mg Ca/8 fl. oz., and that the fortified orange juice can maintain at least about 65% of the initial calcium level in solution after about 12 weeks at about 4° C. Maintenance of the calcium level (about 98%) was enhanced by the use of a beverage stabilizer (maltodextrin).

Table 3-5 shows results of studies of the impact of pasteurization on calcium concentration in solution of commercially-available apple juice fortified with TCC.

TABLE 3-5

Calcium Solubility Study in Pasteurized Apple Juice

| Calcium Fortification System | Pasteurization Temperature (F.) | Pasteurization Hold Time | Calcium Content mg Ca/8 fl. oz. | Percent loss |
|---|---|---|---|---|
| Extruded TCC with Maltodextrin | N/A | initial | 387 | N/A |

TABLE 3-5-continued

Calcium Solubility Study in Pasteurized Apple Juice

| Calcium Fortification System | Pasteurization Temperature (F.) | Pasteurization Hold Time | Calcium Content mg Ca/8 fl. oz. | Percent loss |
|---|---|---|---|---|
| Extruded TCC with Maltodextrin | 205 | 10 seconds | 387 | NC |

TABLE 3-5-continued

Calcium Solubility Study in Pasteurized Apple Juice

| Calcium Fortification System | Pasteurization Temperature (F.) | Pasteurization Hold Time | Calcium Content mg Ca/8 fl. oz. | Percent loss |
|---|---|---|---|---|
| Extruded TCC with Maltodextrin | 205 | 10 minutes | 374 | 3.4 |
| Extruded TCC | N/A | initial | 390 | N/A |
| Extruded TCC | 205 | 10 seconds | 385 | 1.3 |
| Extruded TCC | 205 | 10 minutes | 340 | 12.9 |

Table 3-5 indicates a TCC prepared according to Example 1 was relatively impervious to precipitation during pasteurization when dissolved in apple juice.

Table 3-6 shows results of studies of the impact of pasteurization on calcium concentration in solution of commercially-available orange juice fortified with TCC.

TABLE 3-6

Calcium Solubility Study in Pasteurized Orange Juice

| Calcium Fortification System | Pasteurization Temperature (F.) | Pasteurization Hold Time | Calcium Content mg Ca/8 fl. oz. | Percent loss |
|---|---|---|---|---|
| Extruded TCC with Maltodextrin | N/A | initial | 401 | N/A |
| Extruded TCC with Maltodextrin | 205 | 10 seconds | 398 | 0.75 |
| Extruded TCC with Maltodextrin | 205 | 10 minutes | 253 | 36.91 |
| Extruded TCC | N/A | initial | 408 | N/A |
| Extruded TCC | 205 | 10 seconds | 408 | NC |
| Extruded TCC | 205 | 10 minutes | 249 | 38.97 |

Table 3-6 indicates the TCC prepared according to Example 1 was relatively impervious to precipitation during short pasteurization times when dissolved in orange juice.

EXAMPLE 4

Crystallinity of Tricalcium Citrate

TCC samples prepared according to Examples 1-2 and comparative TCCs available from commercial vendors, were subjected to X-ray scattering. All of the samples were run using the same method and sample preparation. A 1.5 mm glass capillary tube was filled with the tricalcium citrate sample. The capillary tube was sealed and placed in copper tubing used to hold the sample on the X-ray machine. The samples were scanned using Copper radiation over a 30 degree 2θ for 15 minutes. The x-ray scatter was collected using a Beryllium detector plate. The resulting scatter was integrated over 2θ and produced a graph of intensity of scatter versus 2θ. The peaks of these graphs are summarized in Table 4-1.

Figure 4A:
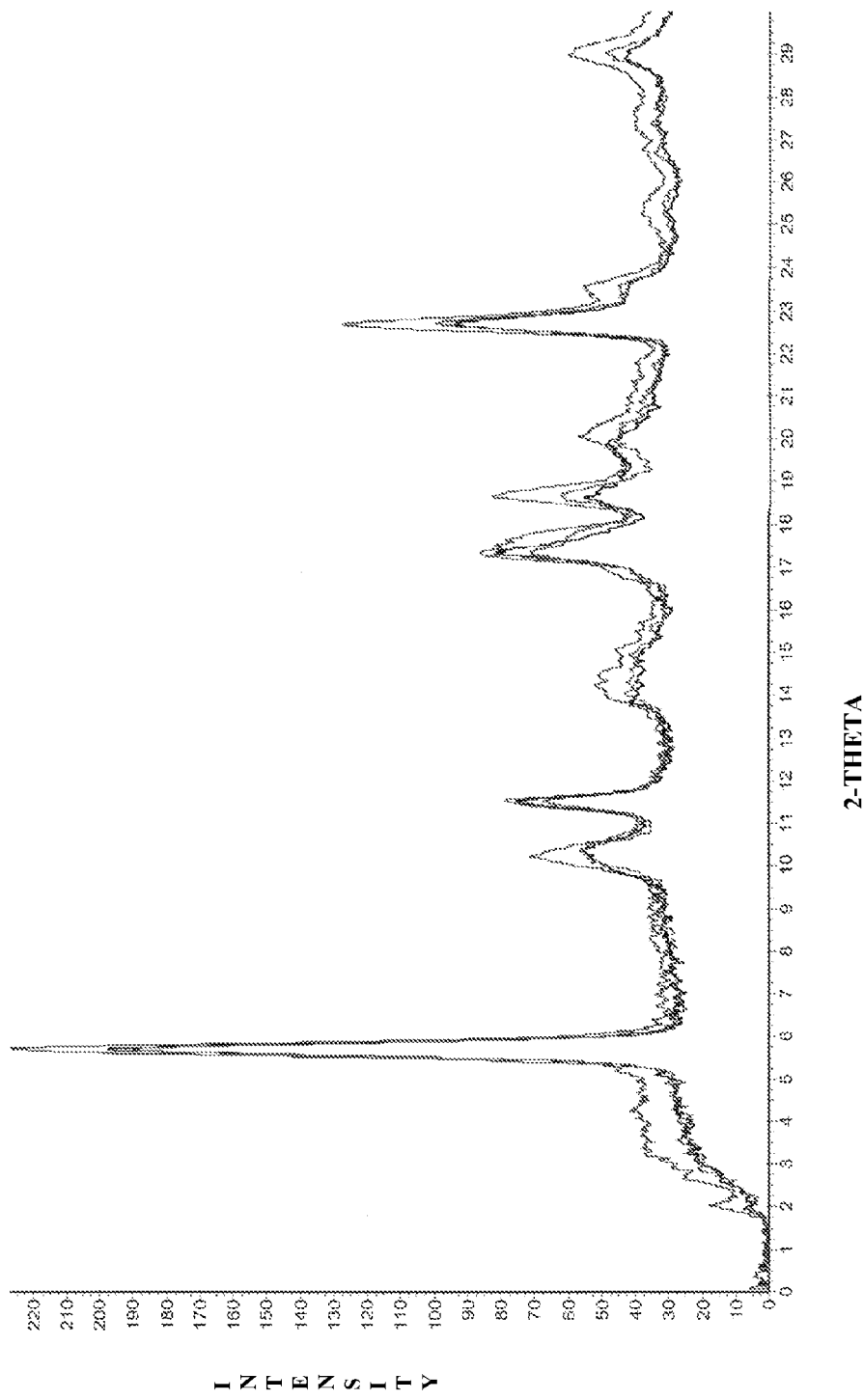
FIG. 4A shows X-ray powder diffraction patterns for comparative tricalcium citrate samples.
Figure 4B:
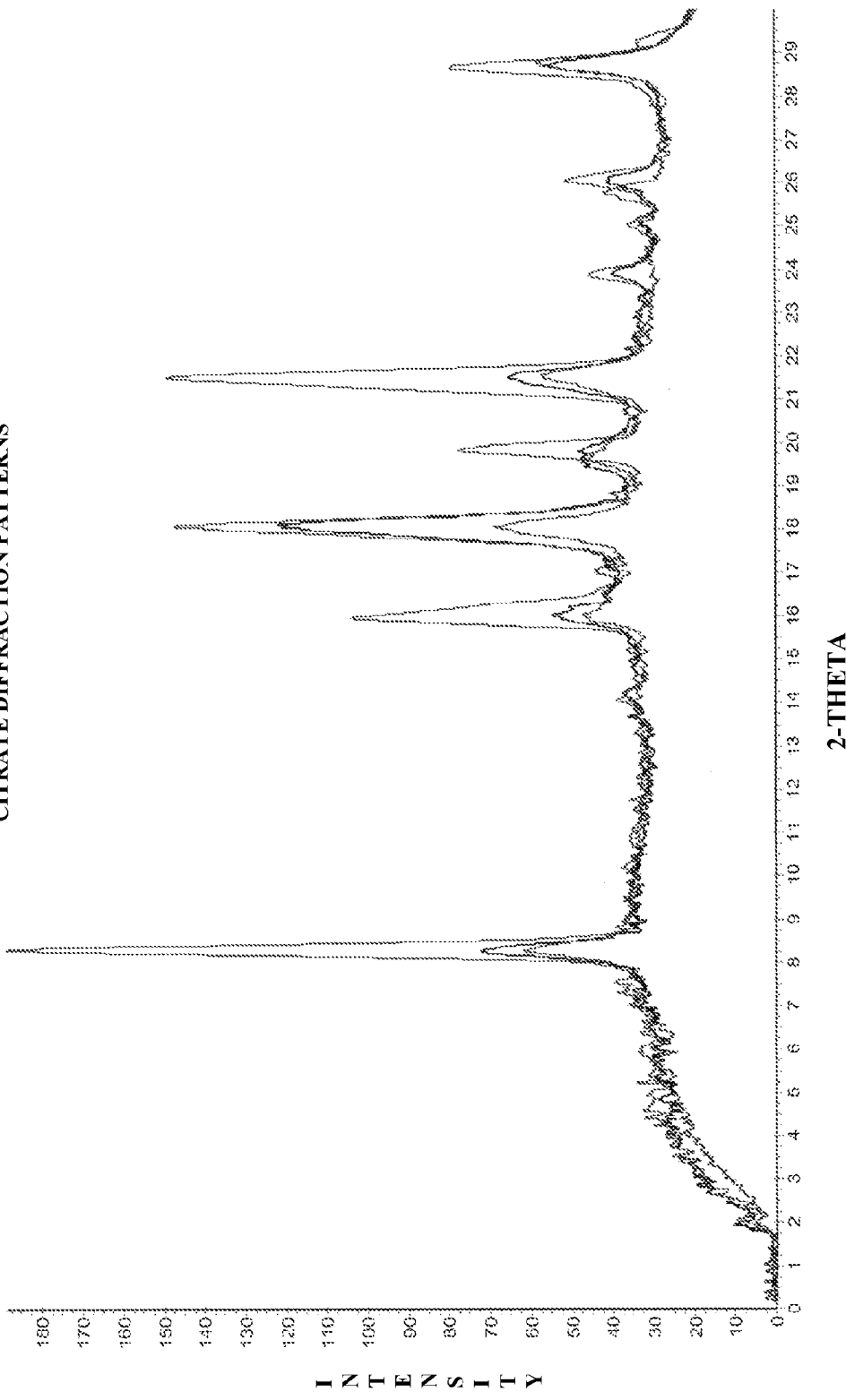
FIG. 4B shows X-ray powder diffraction patterns for tricalcium citrate samples produced according to Examples 1 or 2 of the present specification. The different locations and intensities of peaks are apparent.

In summary, all of the comparative tricalcium citrates (prepared in water solutions) have a distinct crystalline structure that produced a signature diffraction graph with peaks at 2θ of 5.686 (0.003221), 10.26 (0.01458), 11.49 (0.002629), 14.05 (0.1603), 14.89 (0.1556), 17.40 (0.06422), 18.66 (0.01010), 19.96 (0.2104), 22.72 (0.00596). Standard deviations for the 2-theta values are given in parentheses. The high temperature reacted tricalcium citrates according to Examples 1-2 have a distinctly different crystalline structure than the comparative tricalcium citrate samples. The diffraction graphs for the tricalcium citrates of Examples 1-2 have peaks at 2θ of 8.236 (0.02417), 16.02 (0.05443), 17.97 (0.03134), 19.75 (0.03062), 21.42 (0.02401), 25.74 (0.1259), 28.65 (0.08219). Standard deviations for the 2-theta values are given in parentheses. Therefore, it can be concluded that the tricalcium citrate of Examples 1-2 has a different crystalline structure than the comparative tricalcium citrates produced in a water solution. A comparison of the X-ray diffraction patterns for commercially produced tricalcium citrate and high temperature reacted tricalcium citrate are seen in FIGS. 4A-4B.

TABLE 4-1

X-ray Diffraction Pattern Data of Comparative TCC and Examples 1-2 TCC

| Sample | 2 Theta Value | Standard Deviation | Intensity |
|---|---|---|---|
| Comparative Tricalcium Citrate Tetrahydrate | 5.686 | 0.003221 | large, sharp peak |
|  | 10.26 | 0.01458 | medium peak |
|  | 11.49 | 0.002629 | medium, sharp peak |
|  | 14.05 | 0.1603 | small doublet with 14.89 |
|  | 14.89 | 0.1556 | small doublet with 14.05 |
|  | 17.4 | 0.06422 | medium peak |
|  | 18.66 | 0.0101 | medium, sharp peak |
|  | 19.96 | 0.2104 | small peak |
|  | 22.72 | 0.00596 | medium, sharp peak |
| Extruded Tricalcium Citrate Tetrahydrate | 8.23 | 0.0196 | medium peak |
|  | 16.01 | 0.05861 | medium peak |
|  | 17.97 | 0.02671 | large peak |
|  | 19.74 | 0.02697 | small peak |
|  | 21.42 | 0.02446 | medium peak |
|  | 25.75 | 0.127 | small peak |
|  | 28.67 | 0.08475 | medium peak |
| Reactive Agglomerated Tricalcium Citrate Tetrahydrate | 8.274 | 0.01234 | large peak |
|  | 16.03 | 0.003679 | medium peak |
|  | 17.98 | 0.06206 | medium peak |
|  | 19.76 | 0.03917 | medium peak |
|  | 21.44 | 0.01364 | large peak |
|  | 25.68 | 0.1263 | small peak |
|  | 28.66 | 0.07839 | medium peak |

Comparative and Exemplary TCCs were analyzed for organic acid content. A sample each of Tate & Lyle fine granular citric acid, Jungbunzlauer Tricalcium Citrate, Mallinckrodt Tricalcium Citrate, Tate & Lyle Tricalcium Citrate, Example 1 Tricalcium Citrate, and Example 2 Tricalcium Citrate underwent organic acid content determination by chromatography. Table 4-2 shows the results of the organic acid analysis. The tricalcium citrates of Examples 1-2 had similar organic acid profiles as the comparative tricalcium citrate samples.

TABLE 4-2

Organic Acid Content of Tricalcium Citrate Samples

| Sample | Organic Acids | | | | |
| --- | --- | --- | --- | --- | --- |
| | Lactate ppm as-is | Formate ppm as-is | Malate ppm as-is | Oxalate ppm as-is | Isocitrate ppm as-is |
| Extruded Tricalcium Citrate 1 | <5 | <5 | 110 | <5 | <50 |
| Extruded Tricalcium Citrate 2 | <5 | <5 | 145 | <5 | <50 |
| Extruded Tricalcium Citrate with 10% SD10 | <5 | <5 | 110 | <5 | <50 |
| Extruded Tricalcium Citrate (2nd run) | <5 | <5 | 175 | <5 | <50 |
| Extruded Tricalcium Citrate with 10% SD10 (2nd run) | <5 | <5 | 190 | <5 | <50 |
| Tate & Lyle Fine Granular Citric Acid | <5 | <5 | 315 | <5 | <50 |
| Jungbunzlauer Tricalcium Citrate | <5 | <5 | 170 | <5 | <50 |
| Mallinckrodt Tricalcium Citrate | <5 | <5 | <100 | <5 | <50 |
| Tate & Lyle Tricalcium Citrate | <5 | <5 | 170 | <5 | <50 |
| Extruded Tricalcium Citrate (2nd run) | <5 | <5 | 180 | <5 | <50 |
| Extruded Tricalcium Citrate with 10% SD10 (2nd run) | <5 | <5 | 190 | <5 | <50 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions, methods, and steps or sequences of steps of the methods described herein without departing from the concept, spirit and scope of the invention as defined by the appended claims.

What is claimed is:

1. A method of preparing a composition comprising tricalcium citrate, comprising:
   (i) blending about 4 mole parts to about 2 mole parts calcium as calcium salt and about 2 mole parts anhydrous citric acid or citric acid monohydrate, to yield blended calcium salt and citric acid; and
   (ii) melting the blended calcium salt and citric acid, in a low-water environment, to allow formation of the tricalcium citrate.

2. The method of claim 1, wherein the tricalcium citrate has an X-ray powder diffraction pattern comprising peaks at 2-theta ($2\theta$) values of about 8.236, about 16.02, about 17.97, about 19.75, about 21.42, about 25.74, and about 28.65.

3. The method of claim 1, further comprising milling the tricalcium citrate.

4. The method of claim 1, wherein the melting step is performed in an extruder.

5. The method of claim 1, wherein the melting step comprises heating at a temperature from about 175° C. to about 185° C.

6. The method of claim 1, further comprising blending a beverage stabilizer with the tricalcium citrate.

7. The method of claim 6, wherein the beverage stabilizer is maltodextrin, sucrose, glucose, dextrose, fructose, high fructose corn syrup, invert sugar, pectin, algin, starch, hydrolyzed starch, xanthan gum, or two or more thereof.

8. The method of claim 6, wherein up to about 1 part by weight of the beverage stabilizer is blended with about 1 part by weight tricalcium citrate.

* * * * *